(12) United States Patent
Georgi et al.

(10) Patent No.: US 11,039,847 B2
(45) Date of Patent: Jun. 22, 2021

(54) TONGUE CLEANER

(71) Applicant: TSPRO GMBH, Karlsruhe (DE)

(72) Inventors: Matthias Georgi, Lauf (DE); Christoph Geiberger, Lohmar (DE)

(73) Assignee: TSPRO GMBH, Karlsruhe (DE)

( * ) Notice: Subject to any disclaimer, the term of this patent is extended or adjusted under 35 U.S.C. 154(b) by 226 days.

(21) Appl. No.: 15/271,189

(22) Filed: Sep. 20, 2016

(65) Prior Publication Data
US 2017/0007284 A1    Jan. 12, 2017

Related U.S. Application Data

(63) Continuation of application No. PCT/EP2015/055770, filed on Mar. 19, 2015.

(30) Foreign Application Priority Data

Mar. 20, 2014  (DE) .......................... 202014002456.1
Jan. 28, 2015   (DE) .......................... 202015000686.8

(51) Int. Cl.
*A61B 17/24*     (2006.01)
*A61C 17/08*     (2006.01)
(Continued)

(52) U.S. Cl.
CPC ........ *A61B 17/244* (2013.01); *A46B 15/0053* (2013.01); *A46B 15/0081* (2013.01); *A61C 17/04* (2013.01); *A61C 17/08* (2019.05); *A46B 17/08* (2013.01); *A61B 2017/00862* (2013.01); *A61B 2217/005* (2013.01)

(58) Field of Classification Search
CPC .................. A61B 17/24; A61B 17/244; A61B 2017/00862; A61B 2217/005; A46B 15/0081; A46B 15/0055; A46B 15/0067; A46B 15/0069; A46B 16/0075; A46B 15/0097; A46B 9/005; A46B 3/22; A46B 11/063; A46B 17/08; A61C 19/063; (Continued)

(56) References Cited

U.S. PATENT DOCUMENTS 1,983,601 A * 12/1934 Conn ...................... A61B 17/24
                                                                601/137
2,218,072 A * 10/1940 Runnels ............... A61B 17/244
                                                                15/110
(Continued)

FOREIGN PATENT DOCUMENTS

CN     1809301 A      7/2006
EP     0958787 A1    11/1999
(Continued)

OTHER PUBLICATIONS

International Search Report Application No. PCT/EP2015/055770, dated Jun. 25, 2015, 6 pages.

*Primary Examiner* — Mohamed G Gabr
(74) *Attorney, Agent, or Firm* — Artegis Law Group, LLP

(57) ABSTRACT

The present invention wants to provide an improved tongue cleanser showing an improved cleaning effect. For this, a tongue cleanser is suggested having an essentially disc-shaped body, which is provided on its use-side front surface with a profiling suitable for superficially scraping impurity adherent to the human tongue and which forms a hose connection, which communicates with the profiling.

35 Claims, 8 Drawing Sheets

(51) Int. Cl.
*A46B 15/00* (2006.01)
*A61C 17/06* (2006.01)
*A46B 17/08* (2006.01)
*A61B 17/00* (2006.01)

(58) Field of Classification Search
CPC ....... A61C 3/005; A61C 5/62; A61C 17/0208; A61C 17/0214; A61C 17/04; A61C 17/043
See application file for complete search history.

(56) References Cited

U.S. PATENT DOCUMENTS

| | | |
|---|---|---|
| 4,538,631 A | 9/1985 | Prince |
| 5,779,654 A * | 7/1998 | Foley .................. A61B 17/244 |
| | | 601/136 |
| 5,984,935 A * | 11/1999 | Welt ..................... A61B 17/244 |
| | | 606/161 |
| 2008/0147104 A1* | 6/2008 | Gatzemeyer ....... A46B 15/0055 |
| | | 606/161 |
| 2008/0208228 A1* | 8/2008 | Mueller ............... A61B 17/244 |
| | | 606/161 |
| 2010/0240003 A1* | 9/2010 | Fritze ..................... A46B 9/005 |
| | | 433/80 |
| 2011/0151404 A1* | 6/2011 | Dombrowski ......... A46B 15/00 |
| | | 433/96 |
| 2013/0205922 A1* | 8/2013 | Leventhal ................. B01L 3/18 |
| | | 73/864.01 |

FOREIGN PATENT DOCUMENTS

| | | |
|---|---|---|
| FR | 468322 A | 7/1914 |
| WO | 9842264 A1 | 10/1998 |
| WO | 2004/112538 A1 | 12/2004 |
| WO | 2006074911 A1 | 7/2006 |

* cited by examiner

TONGUE CLEANER

CROSS-REFERENCE TO RELATED APPLICATIONS

The present application is a continuation of the PCT application titled, "TONGUE CLEANER," filed on Mar. 19, 2015 and having application number PCT/EP2015/055770. This international application claims priority to the German patent application titled, "TONGUE CLEANER," filed Jan. 28, 2015 and having application number 20 2015 000 686.8 and the German patent application titled, "TONGUE CLEANER," filed on Mar. 20, 2014 and having application number 20 2014 002 456.1. The subject matter of these related applications is hereby incorporated herein by reference.

The present invention relates to a tongue cleanser.

These days, tongue cleansers for the human oral cavity generally are in use. They are inter alia developed on the back side of tooth brushes, usually in the form of nubs made of a soft elastic plastic, usually TPE, and provided as injection mold on the back side of the tooth brush base body made of PP. Thereby, the idea is pursued to simultaneously during brushing the teeth, also to allow the back side of the tooth brush to act at the tongue, in order to scrape impurity adherent there, as for example dead cells or food particles and to remove the same in the scope of the tooth brushing from the oral cavity. Tongue cleansers are further known as only acting as such, i.e. as not comprising filament bristles of a tooth brush. They are more or less configured as manual tooth brushes and comprise at their use-side end a pad provided with nubs, which is arranged on a head being part of the base body of the tongue cleanser.

The present invention wants to provide an improved tongue cleanser. Thereby, the present invention in particular wants to provide a tongue cleanser showing an improved cleaning effect.

In order to solve this problem, with the present invention, a tongue cleanser with the features of claim 1 is indicated. This tongue cleanser basically has a disc-shaped body. The disc-shaped body is characterized by the fact that it comprises a use-side, basically disc-shaped front surface. This front surface basically comprises a disc-shaped, i.e. even extension so that it may be attached preferably flat to the surface of the tongue. On the front surface, a profiling is provided for the tongue cleanser according to the invention. This profiling is suitably configured in order to scrape impurity adherent at the human tongue's surface. For this, the profiling usually comprises nubs and/or ribs, by which said impurity can be scrapped. In order to fulfil the profiling of the tongue cleanser according to the invention, all known configurations, in particular those in connection with tongue cleansers for tooth brushes may be used. Furthermore, the body is equipped with a hose connection. This hose connection usually is located below, at best at the height of the use-side front surface. Specifically, the hose connection usually does not surpass the front surface so that a careful cleaning of the human tongue is allowed. The hose connection regularly merges uninterruptedly the front surface and preferably sideways routes therefrom, i.e. extends with its longitudinal axis parallel to a plane, in which basically, the front surface is located. The hose connection is provided in a way that it communicates with the profiling. For this, in the body one or multiple channels are provided, through which usually ventilation openings, which are provided inside the profiling, communicate with the hose connection. Via a suction hose connected to the hose connection, correspondingly, during acting of the tongue cleanser, dissolved impurity may be discharged by means of the suctioning.

By this embodiment, an improved cleaning effect is achieved. The tongue cleanser according to the invention due to its profiling is not only suitable for dissolving impurity from the tongue. Rather, via a suction hose connected to the connection hose, the thus dissolved impurity may be purposefully and effectively discharged from the oral cavity.

Thereby, specifically, the use of the tongue cleanser according to the invention in the professional dental care is aimed. In the professional dental care and/or hygiene, the tongue cleanser according to the invention via the hose connection is connected to a suction hose, which anyway is usually available during the dental treatment and/or prophylaxis.

Normally, the tongue cleanser is a one-way part. It may be configured as disposable part. Alternatively, it is also possible to sterilize the tongue cleanser. Preferably, the tongue cleanser is produced as simple one-piece injection-molded part. In other words, all subsequently even further clarified components of the tongue cleanser are formed by a consistent injection-molded body. For the production of the tongue cleanser, the use of one single plastic component is sufficient. This may be a hard component or a soft component. Preferably, the tongue cleanser may also be produced by means of multi-component injection molding. Thus, at a PP or PE and/or PA base body, an injection-molding made of a softelastic material may be inserted. This soft-elastic plastic, for example TPE, may completely or partly form the profiling. It may also shape a sealing for the connection of the suction hose to the hose connection. Moreover, the soft-elastic components may also coat such regions of the base body, which in the scope of the usual use, most likely strike the sensitive oral mucosa, in order to protect the same.

In view of the confined space conditions in the human oral cavity, the body is configured as flat as possible. Preferably, the body basically is configured plate-shaped and provided with a cylinder nozzle, which is shaping the hose connection. Preferably, his cylinder nozzle rearwardly surpasses the basically plate-shaped, i.e. flat body of the tongue cleanser. The cylinder nozzle basically is arranged flush with the use-side front surface of the body. Preferably, the cylinder nozzle basically merges uninterruptedly a circumferential edge, which entirely encompasses the plate-shaped body.

Preferably, the hose connection communicates with one or more channels inside the body, which continue the suction line connected to the tongue cleanser in the tongue cleanser's body and further lead it to the profiling. In view of a possibly simple arrangement, an outlet duct extending in the body in longitudinal direction of the hose connection is provided, into which the hose connection ends. The hose connection and the outlet duct usually are provided one after another in longitudinal direction, particularly preferred co-axially to one another.

In order to prevent the tongue cleanser from attaching itself, the outlet duct communicates with a ventilation opening. This ventilation opening is a further opening, which is not the hose connection. Rather, the ventilation opening is usually located in longitudinal direction of the outlet duct and/or the hose connection at the side opposite to the hose connection, specifically, at the end face of the outlet duct. The ventilation opening is measured in a way that during the normally negative acting suction pressing, the tongue cleanser is held adjacently with a certain retention force at the tongue. Thus, the tongue cleanser may be moved at any time relatively to the tongue and may be removed from the same.

The hose connection, the outlet duct, and the ventilation opening are arranged in axial direction of the cylinder nozzle, preferably one after another. Correspondingly, the channel formed by the outlet duct and the cylinder nozzle usually permeates the body concentrically. In view of a possibly flat, i.e. thin design of the actual body, the outlet duct is formed in a conically tapered tube section, the end with the greater diameter of which connects the hose connection. With a greater distance from the hose connection, correspondingly, the effective flow area of the outlet duct decreases. However, even at the end of the outlet duct, its diameter is considerably greater than the effective flow diameter of the ventilation opening. This is usually located at the height of the outer contour of the body. In other words, the conically tapered pipe end at least unilaterally ends basically flush with the outer contour of the use-side surface. Preferably, the ventilation opening thereby is located inside the edge, which entirely encompasses the body. At the opposite side usually the cylinder nozzle protrudes in order to shape the pipe connection. Beyond this cylinder protruding from the body and the tube section, the body is disc-shaped, usually elliptic or with a circular base form.

According to a preferred further embodiment of the invention, the profiling is formed by fins, which extend parallel to one another. Thereby, the tongue cleanser comprises for example between four to six fins. The fins usually extend perpendicularly to the outlet duct and/or the hose connection, i.e. the cylinder nozzle.

The fins preferably route from a fin base. Thereby, the fins are thinner than the fin base. The fin base correspondingly is widened compared with the fins. In a sectional view through a fin, correspondingly, an L-shaped cross-section occurs, whereby the base of the L is formed by the widened fin base and the actual fin protrudes therefrom as a bar. The width of the fin base may be up to 4 to 8 times the width of the fin. As width here, the extension parallel to the use-side surface in a cross-sectional view through the fin and/or the fin base is understood. Regarding the preferred embodiment, according to which the fins extend perpendicularly to the hose connection, said sectional view runs in longitudinal extension direction of the hose connection, i.e. the cylinder nozzle.

In view of an effective cleaning of the tongue surface, multiple fins and/or fin bases are provided. These are usually arranged one after another in longitudinal direction of the outlet duct. They usually extend respectively parallel to each other. Correspondingly, a kind of grate occurs, whereby usually only the free end surfaces of the fins reach the surface to be attached to the tongue, whereas the fin bases with a distance thereto and positioned inwardly, are formed by the body. Thereby, the design of the fin bases usually is the elasticity and/or the restoring force of the individual fins varies. Every fin and its associated fin base are usually configured as a monoblock part and are securely connected to one another. Thereby, every fin base in its extending direction may have a changing cross-section and/or a changing cross-sectional form, in order to influence the restoring behavior of its associated fin. Thus, the strength of the fin, i.e. usually its extension perpendicular to the use-side front surface in extension direction of the fin base, may increase or decrease. Furthermore, fins of different position inside the use-side front surface may be assigned to different functionalities. For this, according to a preferred further embodiment, it is suggested to decreasingly form the strength of the fin base in extension direction of the hose connection towards the center. In other words, directly adjacent to the hose connection and/or at the opposite end, i.e. in extension direction of the hose connection at the edge of the body, the fin base has a greater strength and therefore is more rigid than a fin base, which more or less is located in the center of the use-side front surface in extension direction of the hose connection, i.e. has more or less the same distance to the end face of the outlet duct and the opposite end of the same, there, where the outlet duct ends into the hose connection.

Preferably, at least one of the front or rear walls of the fin is convex bent formed. In other words, in a sectional view in extension direction of the hose connection, an at least unilateral convexity of the fin occurs. Thereby, the fins usually widen in the direction of their fin foot. In other words, the fins at their free end have a smaller width than at the transition of the fin to the fin base. As width thereby, the measuring is to be understood, which extends in a sectional view in extension direction of the hose connection to this extension direction of the hose connection. The convex bent front and rear wall of the fin usually is the wall, which is protruded from the wider fin base, which is associated to the respective fin. The other side usually ends flush with the fin base and preferably is linearly running configured.

The end surfaces of the fins, i.e. the free, usually use-side front surface of the disc-shaped body, making up end surfaces of the fins are preferably convex bent. In its extension direction, the fin correspondingly is in the middle area, usually higher than at its edge, where the fin usually uninterruptedly merges the outer edge of the disc-shaped body. Thus, every fin separately adheres to a convex end surface. The bending of the middle fins thereby is usually stronger than the bending of the fins at the end. The end surfaces of all fins are preferably in a spherically formed shell surface. The lateral ends of all fins usually end flush with the edge encompassing the use-side surface. The edge defines the undermost plane of the use-side surface. From this edge, the fins protrude, which respectively are lying inside the above mentioned spherical shell surface with their bent end surfaces. The spherical shell surface thereby usually contains the surface of the entirely encompassing edge.

According to a preferred embodiment, between the rear side of a fin and a fin base associated to the fin provided adjacently thereto, there is provided at least one outlet duct communicating with the vent opening. The vent opening thereby is particularly located in elongation of the longitudinal extension of the hose connection. Usually, all vent openings are located on one axis, which is predetermined by the longitudinal extension of the cylinder nozzle, i.e. they are lying on a median longitudinal axis of the cylinder nozzle. Usually, a drain channel leads to such a vent opening. The drain channel is provided between a fin and a fin base, whereby said fin base is associated to another fin, which is provided adjacently to the aforementioned fin. The vent opening correspondingly is located between a rear wall of the fin and an end surface of a fin base, which is associated to the respectively adjacent fin. Bilaterally to every vent opening, there are respectively provided drain channels, which extend to the respective edge.

The drain channel usually is configured in direction of the vent opening. In other words, a lateral edge of the drain channel is usually located higher than the end surface of the drain channel, which is provided adjacently to the vent opening. Thereby, the drain channel usually is offset inwardly to the use-side surface of the fin base. The fin base merges relatively sharp-edged, i.e. perpendicularly to the drain channel, whereby below the cleaning active front surface formed by the end surfaces of the fins, a profiling between the fin base and the drain channel is established, which if necessary may contribute to cleaning the tongue.

Finally, according to a preferred further embodiment of the present invention, it is suggested to respectively provide vent openings in extension direction of the hose connection before and behind each of the fins. This leads to a very effective discharge of the impurity dissolved by the profiling. Usually, it is provided one more vent opening than fins are present.

Further details of the present invention may be acquired by referring to the following description of an embodiment in conjunction with the drawings, wherein.

Figure 1:
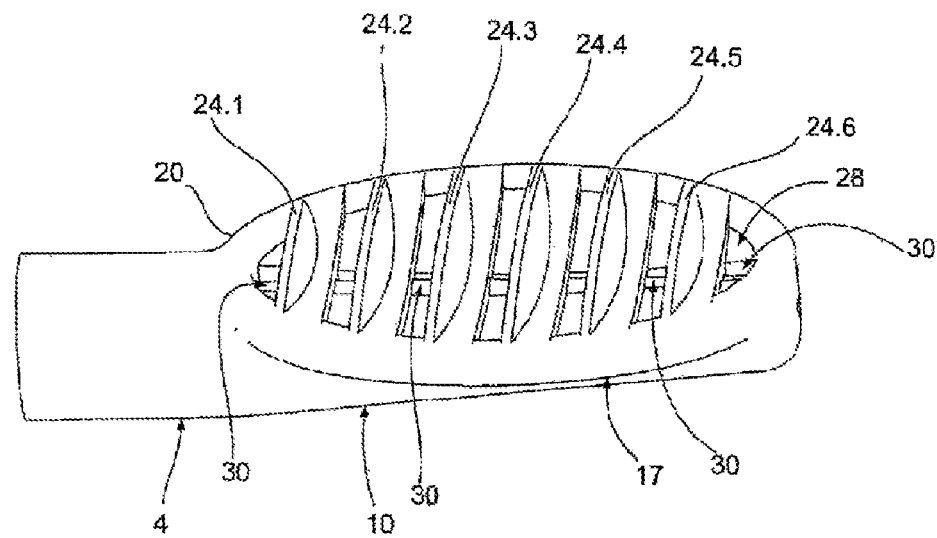
FIG. 1 is a perspective side view of the embodiment.

In these drawings, reference sign 2 characterizes a disc-shaped body 2, which is unilaterally surpassed by a cylinder nozzle 4, which shapes a hose connection 6. The cylinder nozzle 4 pursues in its elongation into an outlet duct 8, which is formed in a conically tapered tube section 10. The tube section 10 and the cylinder nozzle 4 at their outer surface have a smooth contour, i.e. they merge each other uninterruptedly. The tube section 10 runs out at its end opposite to the cylinder nozzle 4 in a front side end wall 12, which is provided with a ventilation opening 14. Regarding the shown embodiment, the hose connection 6, the outlet duct 8, and the ventilation opening 14 are arranged co-axially to one another. Between the hose connection 6 and the outlet duct 8, a ring surface 16 is shaped, which serves the end attachment and sealing of a hose introduced in the hose connection 6.

Figure 2:
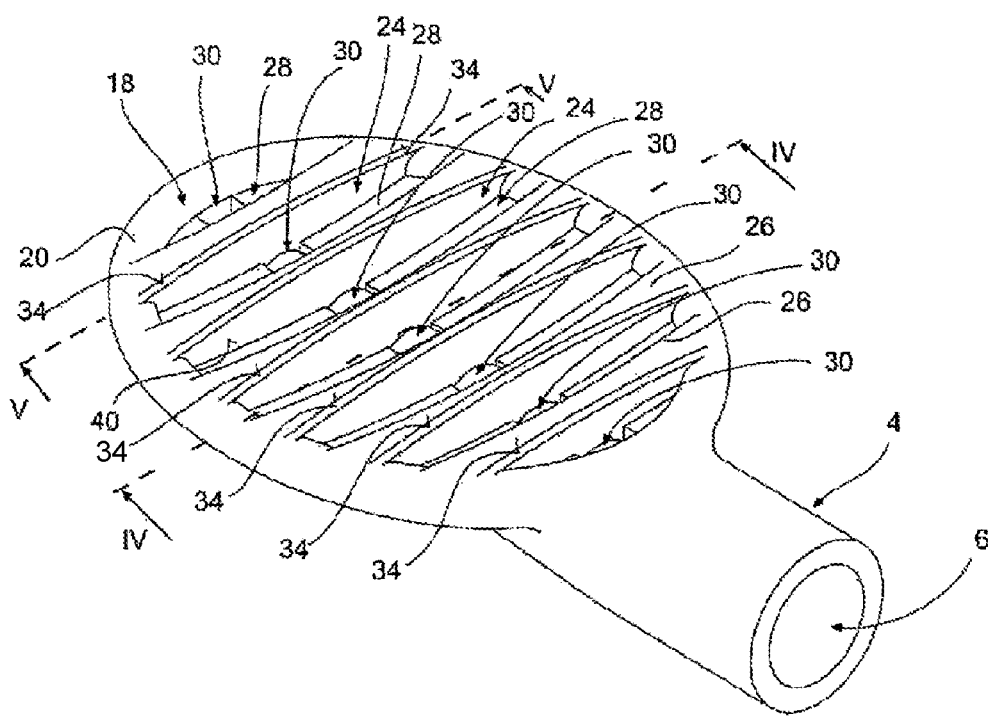
FIG. 2 is a further perspective top view of the embodiment.

As in particular evident in FIG. 2, the disc-shaped body 2 is configured plate-shaped and is only surpassed at the rear side 17 by the cylinder nozzle 4 and the conically tapered tube section 10. A use-side front surface 18 of the disc-shaped body, however, is basically plane, which may also be contributed by the fact that the cylinder nozzle 4 is configured at this front surface 18 flush with an entirely encompassing edge 20 of the disc-shaped body 2. This encompassing edge 20—in the cross-sectional view of the edge 20—has an even convex curve in order to exclude harm of the sensitive oral mucosa.

Inside the edge 20, there is a profiling 22 consisting of fins 24, which elevate from a fin base 26. Between the fin base 26 and a fin 24 with a different fin base 26, there is a drain channel 28 leading to a vent opening 30. All vent openings 30 are provided in elongation of the longitudinal extension of the cylinder nozzle 4/hose connection 6. The drain channel 28 respectively is formed by a relatively thin-walled bar 32, which is arranged between a fin base 26 and another fin 24, which is provided adjacently thereto.

Figure 6:
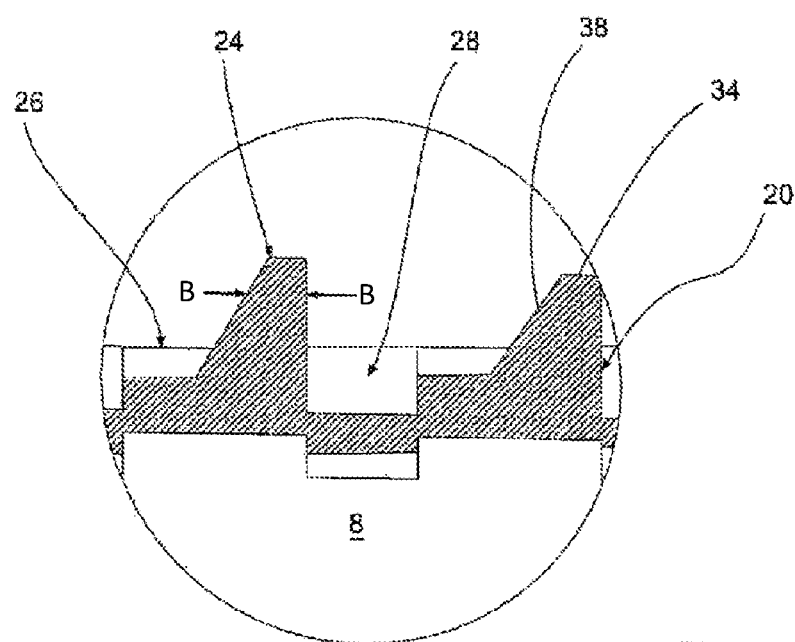
FIG. 6 is a cutaway side view along the line VI-VI according to the view in FIG. 4 for another embodiment with linearly running rear walls of the fins.
Figure 7:
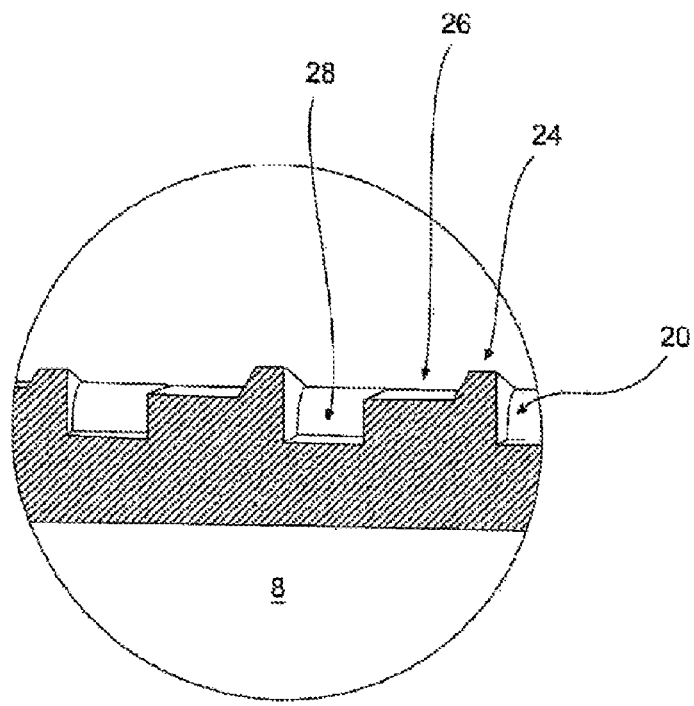
FIG. 7 is a cutaway side view along the line VII-VII according to the view in FIG. 4 for another embodiment with linearly running rear walls of the fins.
Figure 8:
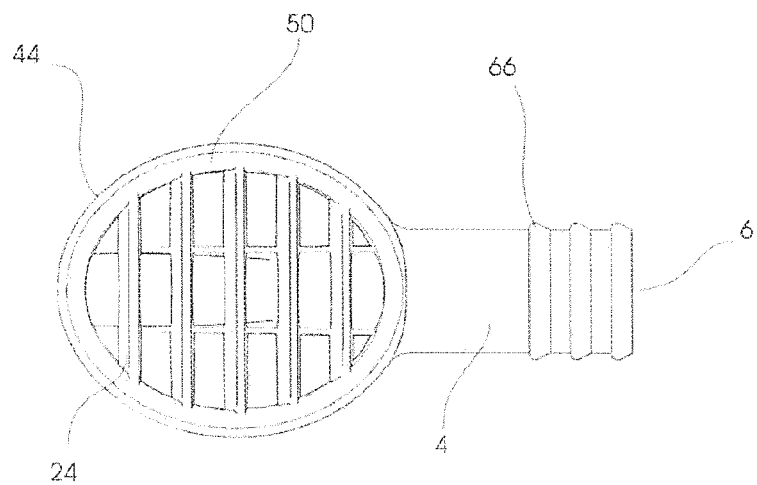
FIG. 8 is a top view of a second embodiment of the present invention.

As evident, the fins 24 extend perpendicularly to the extension direction of the cylinder nozzle 4 of the hose connection 6. The fins 24 and the respectively associated fin bases 26 are formed L-shaped in the cross-section. Thus, the fins and their associated fin base run strictly parallel to one another. As illustrated by the sectional views according to FIG. 3 and FIG. 6, the fin base 26 is widened compared to the fin 24 associated thereto. The width of the fin 24 is sketched in FIG. 3B. The fin 24 has a smaller width than the fin base 26. Thereby, essentially an L-shaped cross-sectional arrangement of fin 24 and its associated fin base 26 occurs.

Every single fin 24 has a convex bent end surface 34. In other words, the end surface 34 of every single fin 24 routes from the encompassing edge 20 and is configured height flush with the same. The fin 24, however, rises to the middle of the disc-shaped body 2. In other words, the end surface 34 at the height of the outlet duct 8 lies higher than at the edge 20. Moreover, the middle fins 24 have a higher height than the other fins 24. Thereby, an enveloping surface involving the end surfaces 34 occurs, which is designed spherically and which involves the use-side surface of the edge 20. As furthermore evident from FIG. 6, every fin 24 widens to its fin foot 36. The fin 24 therefore is narrower in the area of its end surface 34 relatively to that position, where the fin 24 merges the fin base 26. This widening is mainly configured by a convex bent rear wall 38 of the fins 24. The convex bending at the rear wall 38, however, varies in extension direction of the fin 24. Thus, the convexity of the fin near the edge 20 is smaller than the one in the center, i.e. at the height of the hose connection 6 and/or in axial elongation thereof and on the height of the outlet duct 8. Thus, the width B of the fin 24 continuously increases to its center. Correspondingly, also the fin 24 has its widest section in axial elongation of the hose connection.

While the rear wall 38 of the fin 24 is convex bent, the front wall 40 of the fin 24 runs linearly, whereby an L-shaped cross-section for the unity of fin 24 and associated fin base 26 occurs.

Figure 3:
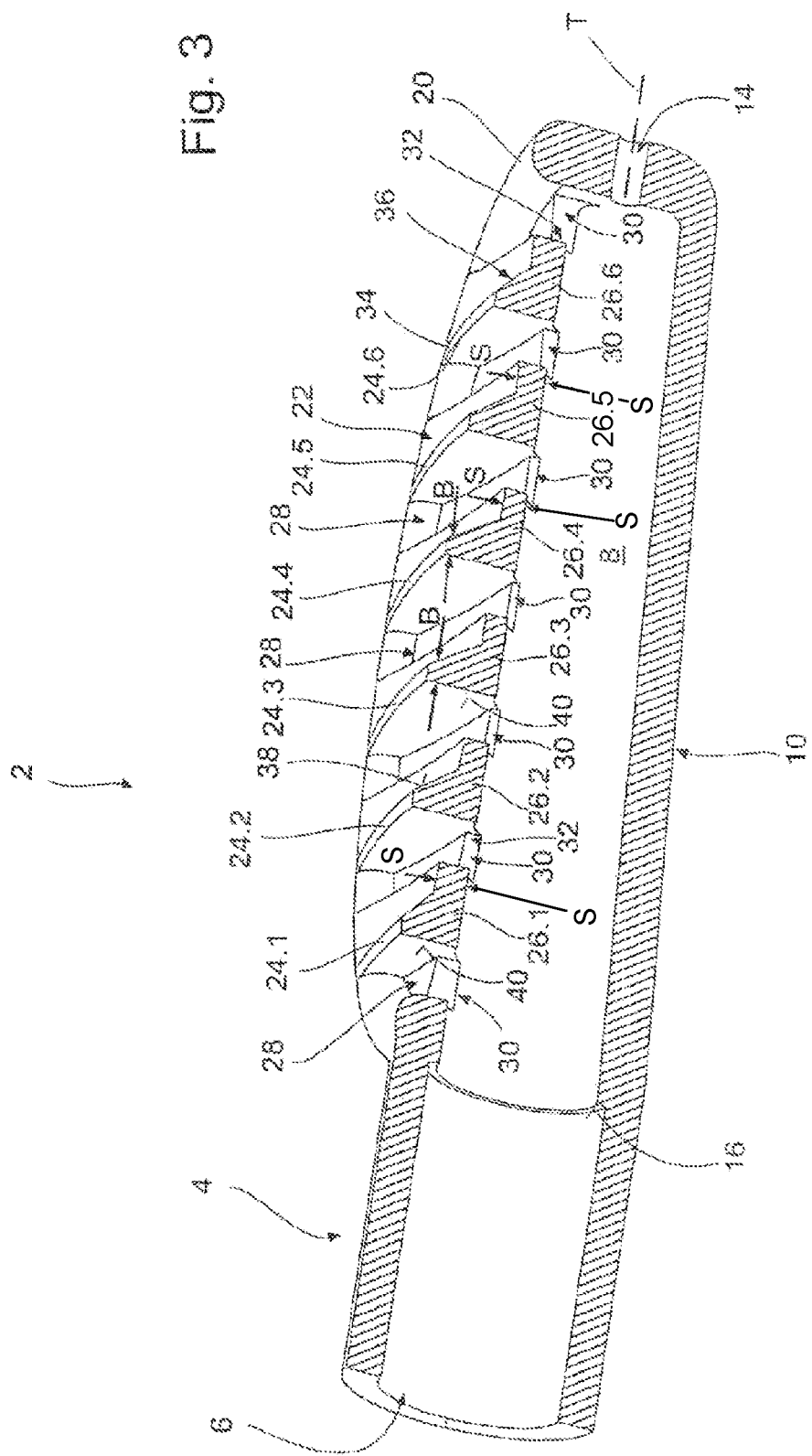
FIG. 3 is a perspective view according to FIG. 1 with a section through the median longitudinal axis.

As in particular derivable from the sectional view according to FIG. 3, the strength S of the fin base 26 varies in extension direction of the hose connection 6. The strength S thereby declines particularly in extension direction of the hose connection 6 to the center of the body 2. Fin bases 26.1 and 26.6 at the edge correspondingly have a stronger strength S than the middle fin bases 26.3 and 26.4.

The fins 24 and the fin bases 26 are provided flush at the end with the edge 20. Correspondingly, at the edge 20, an uninterrupted and smooth contour occurs. The drain channel 28 provided between a fin 24.2 and a fin 24.1 provided adjacently thereto ends below the use-side surface of the edge 20.

Every drain channel 28 leads to the associated vent opening 30 and is centrally divided by the same. The drain channel 28 is shaped inclined, i.e. inclines in the direction of the associated vent opening 30.

As illustrated by the Figures, the shown embodiment had six fins 24 with their associated fin bases 26. However, seven vent openings 30 are provided. Every assembly of fin 24 and fin base 26 is provided at the front side and the rear side between two vent openings 30.

Figure 4:
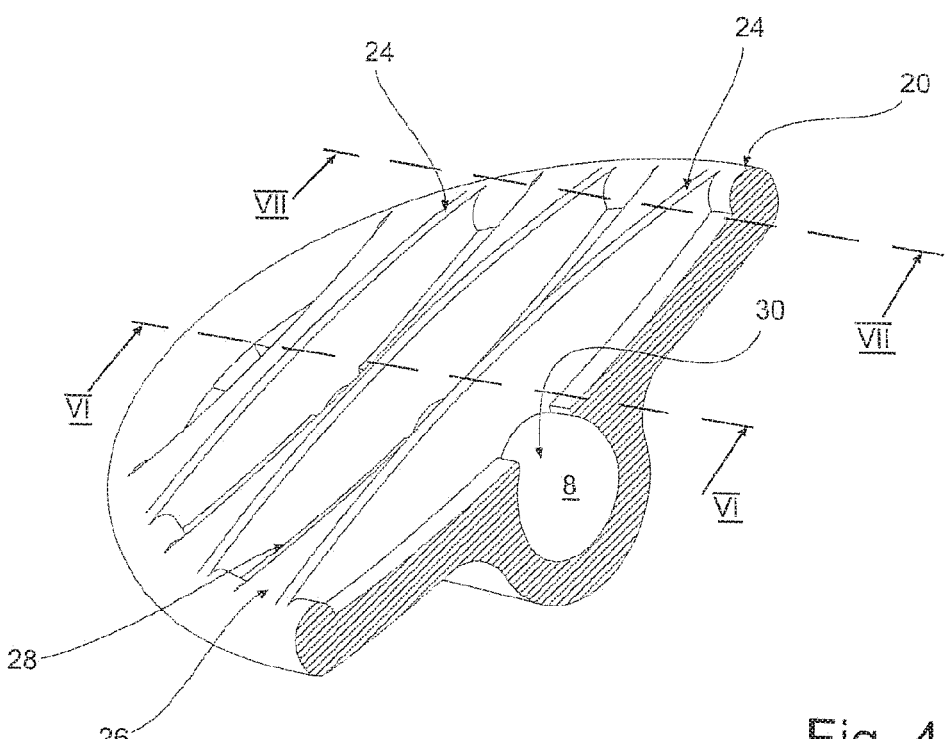
FIG. 4 is a sectional view along the line IV-IV according to the view in FIG. 2.
Figure 5:
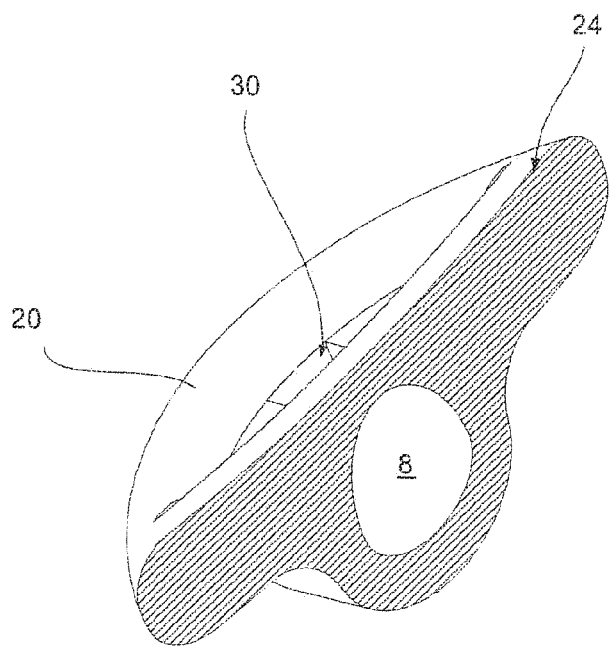
FIG. 5 is a sectional view according to the line V-V according to the view in FIG. 2.

As in particular illustrated by FIG. 4, the disc-shaped body 2 is relatively thin, i.e. configured plate-shaped and only surpassed backwardly by the cylinder nozzle 4 and/or the conically tapered tube section 10. Thus, the shown embodiment may be well introduced to the oral cavity of the human body. The width, i.e. the extension direction of the disc-shaped body 2 in longitudinal direction of the hose connection preferably is between 26 and 33 cm (excluding the cylinder nozzle 4 surpassing the use-side front surface 18). In a direction perpendicular thereto, the front surface 18 has an extension of between 23 cm to 28 cm.

The shown embodiment is produced as injection-molded part. Thereby, the hose connection 6 and the outlet duct 8 are released by a movable core, which is introduced in an injection mold, the dividing plane of which basically extends parallel to the use-side front surface 18 and is located at the height of the largest width of the cylinder nozzle 4. The dividing plane in FIG. 3 is characterized with T. The fins 24 extend perpendicularly to the dividing plane T so that the embodiment made of a uniform injection-molded body illustrated in the Figures after opening may be demolded without further aids.

The second embodiment shown in FIGS. 8 to 14 is a tongue cleanser, which is made by means of two-component injection-molding comprising a soft component characterized with reference sign 42, which is shaped by means of insert-molding of a base body made of a hard component characterized with reference sign 44. The soft component thereby has a Shore hardness A of between 25 and 80 and is preferably made of TPE. The hard component preferably is PP and usually has a Shore hardness A of between 70 and 100. In accordance with the reference sign 44 for the hard component, also the base body formed by the hard component is characterized with this reference sign, whereas reference sign 42 clarifies the soft component and, thus, also the insert-molding. Apart from that, the reference signs used in respect of the first embodiment were maintained—where appropriate.

Figure 12:
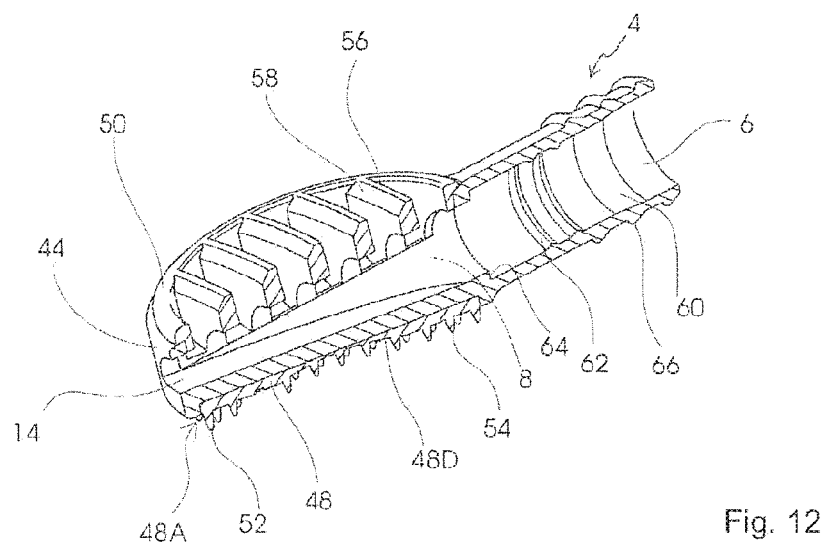
FIG. 12 is a sectional view along the line XII-XII according to the view in FIG. 9.
Figure 13:
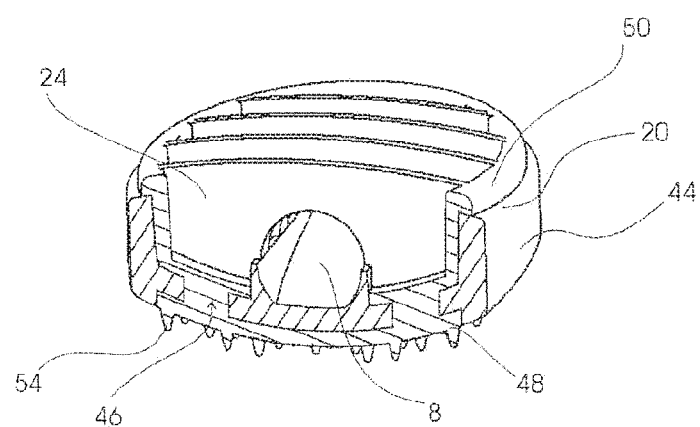
FIG. 13 is a cross-sectional view along the line XIII-XIII according to the view in FIG. 9.

As in particular illustrated by FIGS. 12 and 13, the base body 44 in the area of the disc-shaped body 2 is configured bowl-shaped and presently has several, normally at least one hot-runner injection-molding opening 46. Above this hot-runner injection-molding opening 46, a pad 48 at the rear side 17 is integrally molded with an elastomeric protective edge 50, which surpasses and basically encompasses the edge 20 of the base body 44. The fins 24, as well, are formed of a soft component. Presently, the fins 24 are exclusively formed of the soft component 42. However, also embodiments are conceivable, according to which a frame made of the hard component 49 is coated with a soft component 42 in order to form the fins 24.

Figure 11:
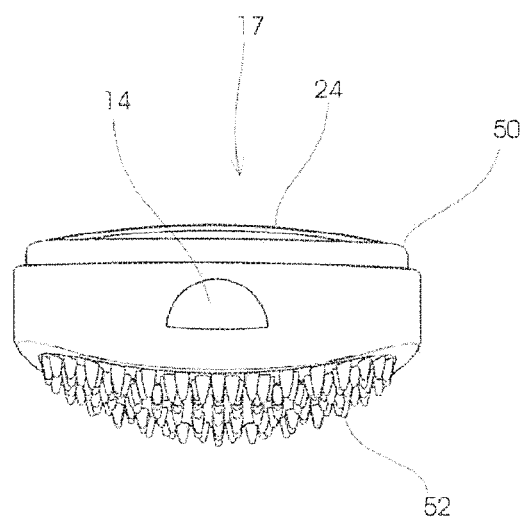
FIG. 11 is a front side view of the second embodiment.

As in particular illustrated by FIG. 11, the pad 48 has a basically even design, which may be slightly bent outwards. Contrary to the first embodiment, this second embodiment lacks of a rearwardly protruded tube section. Rather, the outlet duct 8 is absorbed inside the disc-shaped body 2. Nubs 52, 54 of different length are protruding from the pad 48. The massaging nubs with reference sign 52 are the long nubs, the massaging nubs with reference sign 54 are the short nubs. Presently, the long nubs 52 are approximately twice as long as the short nubs 54. Usually, the nubs 52, 54 may have a height of between 0.5 and 1.5 mm. The nubs 52, 54 may have different configurations. Nubs with a circular cross-section are to be preferred, the diameter of which preferably is between 0.3 and 2.0 mm. The rearward pad 48 with the nubs 52, 54 serves the massage of the tongue surface. With such a pad 48, impurities in the oral cavity may be dissolved, which may afterwards be suck off by the tongue cleanser. With a unique movement through the oral cavity, it is also possible to clean different surfaces, namely those, at which the pad 48 is moved along and those, at which the fins 24 are moved along.

Furthermore, the pad 48 with the nubs 52, 54 may be used as applicator for applying cleansing and disinfection means to the tongue. The pad 48 therefore has a nub field with up to 30 and 80 nubs 52, 54.

For this, the pad 48 has a middle dosing range 48D with a relatively small wall strength on the side of the pad 48 and with relatively long nubs 52, 54 and an application range 48A entirely encompassing the same. The dosage range 48D for example serves applying a care substance to be massaged in. As furthermore illustrated by FIG. 9, at the edge between the dosage range 48D, which is presently shaped circularly, and already in the application range 48A, there may be provided a branding 48B, i.e. a trademark or the like.

Figure 14:
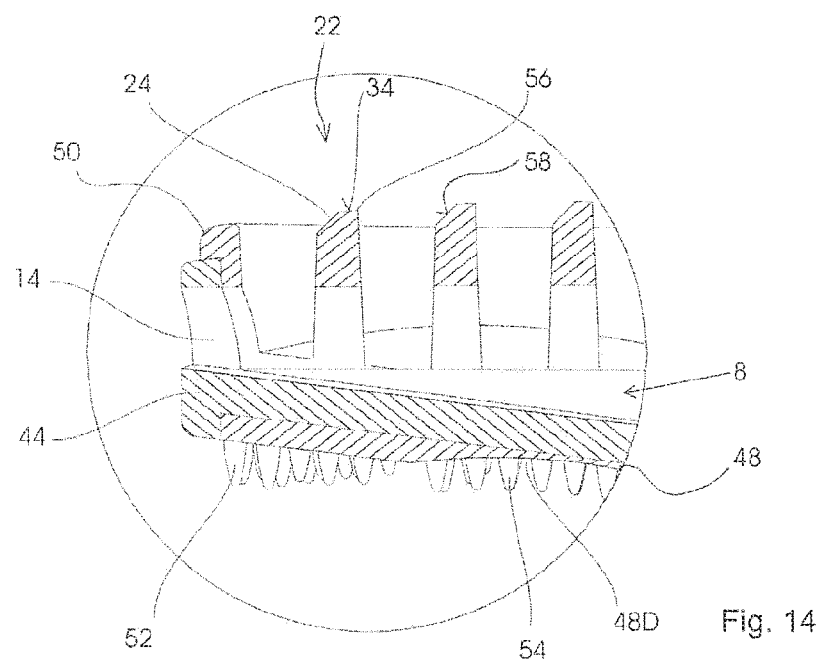
FIG. 14 is a zoomed sectional view of an edge area of the second embodiment.

There may be provided between one and ten fins. Regarding the second embodiment, five fins 24 are realized. As illustrated in FIG. 14, a scraping edge 56 is formed by the profiling 22 of the fins 24, which is shaped at the flank of the fin facing the hose connection 4 between this flank and the end surface 34, as well as an inclined surface 58, which is provided between the end surface 34 and the flank at the fin 24 facing the ventilation opening 14. This configuration has turned out being advantageous for a thorough cleansing during scraping the tongue. Thereby, the scraping edge 56 may remove stubborn impurity from the tongue. The inclined surface 58 improves the discharge of the thus dissolved impurity into the outlet duct 8.

Figure 9:
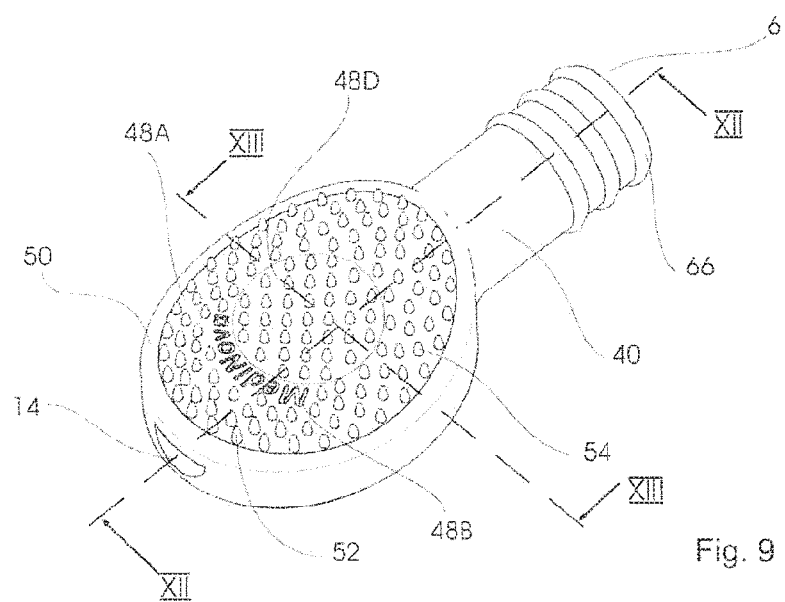
FIG. 9 is a perspective underside view of the second embodiment.
Figure 10:
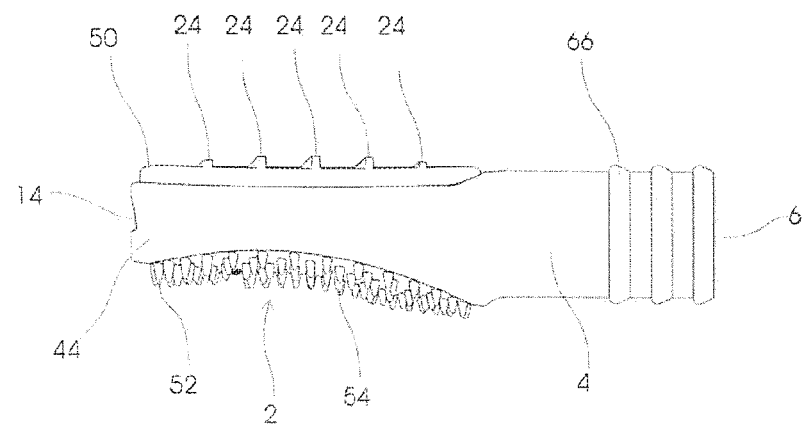
FIG. 10 is a side view of the second embodiment.

As illustrated by FIGS. 9 and 11, the ventilation opening 14 has a sickle-shaped and/or a semicircular cross-section and—as the profile of the outlet duct 8 (compare FIG. 13)—bulges outwardly in direction of the free end of the fins 24. This configuration improves the sucking off of dissolved impurity and prevents amongst others that sucked off secretion may flow back again. The ventilation opening 14 enables an operation of the embodiment without an excessive stress of the tissue surface with a non-adjustable suction pressure, as it is usually available at dental workplaces. Thereby, there is a proportionate relation between the suction surface, i.e. the free surface enclosed inside the edge 20, and the cross-section of the ventilation opening 14. Thereby, the suction surface may be 5 and 50 times larger than the cross-section of the ventilation opening 14. Regarding the second embodiment, as well, the ventilation opening 14 is located in elongation of the outlet duct 8, in order to at any case provide a certain suction pressure at the suction surface, i.e. to position the suction surface between the ventilation opening 14 and the hose connection 6. Thereby, also the effect is achieved that the suction air flow is lead via the tissue surface and, there, shows a functional effect. Nevertheless, the ventilation opening 14 could be provided at another appropriate position. Regarding the shown embodiment, due to the configuration and arrangement of the ventilation opening 14, it is guaranteed that an even, in all areas of the suction surface, an equally strong suction performance is provided.

FIG. 12 illustrates the details of the hose connection 6, which has a lead-in chamfer 60 with a small axial distance from the orifice in order to tightly align the hose, which usually is a standard hose used in the dentistry with a diameter of approximately 6 mm. With a further axial distance from the insertion opening, there are several retaining ribs 62, which entirely clamp and hold the hose inserted there. Furthermore, at the end of the hose connection 6, a stop 64 is provided, at which the insertion movement of the hose comes to an end. The stop 64 qualifies the beginning of the outlet duct 8. This outlet 8 usually merges uninterruptedly the hose attached to the stop 64, i.e. the lumen of the hose. The cylinder nozzle 4 further has several axially spaced handle ribs 66, with which the tongue cleanser for sliding on the hose may be preferably and securely held.

Preferably, between one and three of such handle ribs 66 are provided. As illustrated in FIGS. 12 and 14, the fins 24 are basically configured with identical strength and directly merge the outlet duct 8. The profiling of the fins explained in detail in respect of the first embodiment lacks. Rather, the fins 24 protrude as "ribs" above the outlet duct 8 with a slightly convex bent course perpendicular to the longitudinal extension of the outlet duct 8 via the encompassing protective edge 50, however, merge uninterruptedly this protective edge 50.

What is claimed is:

1. A tongue cleanser having a substantially disc-shaped body, an edge that encompasses the substantially disc-shaped body, a use-side front surface of the edge that is provided with a profiling suitable for superficially scraping impurities adherent at a human tongue, and a surface that is different from the use-side front surface and is provided with a ventilation opening, wherein:
    the tongue cleanser forms a hose connection that communicates with the profiling, and
    the profiling includes:
        a first fin disposed between a first position on the edge and a second position on the edge that is opposite to the first position;
        a second fin substantially parallel to the first fin and disposed between a third position on the edge and a fourth position on the edge that is opposite to the third position; and
        a drain channel disposed between and parallel to the first fin and the second fin, the drain channel being centrally divided by a first vent opening, the first vent opening being located below the use-side front surface of the edge, and the drain channel being continuously inclined from the edge to the first vent opening.

2. The tongue cleanser according to claim 1, wherein the hose connection merges in a longitudinal direction of the hose connection inside the body to form an extending outlet duct.

3. The tongue cleanser according to claim 2, wherein the outlet duct communicates with the ventilation opening.

4. The tongue cleanser according to claim 3, wherein the hose connection, the outlet duct, and the ventilation opening are arranged sequentially in an axial direction of a cylinder nozzle.

5. The tongue cleanser according to claim 2, wherein the outlet duct is formed in a conically tapered tube section, wherein an end of the tube section having a greater diameter connects the hose connection.

6. The tongue cleanser according to claim 2, wherein the profiling has fins, including the first fin and the second fin, extending parallel to one another.

7. The tongue cleanser according to claim 6, wherein the fins extend perpendicularly to at least one of the outlet duct or the hose connection.

8. The tongue cleanser according to claim 6, wherein the fins route from a fin base that is wider than the fins.

9. The tongue cleanser according to claim 8, wherein two or more fins are disposed in a longitudinal direction of the outlet duct.

10. The tongue cleanser according to claim 8, wherein a strength of the fin base increases towards a center in an extension direction of the hose connection.

11. The tongue cleanser according to claim 8, wherein the edge encompassing the substantially disc-shaped body comprises an outer radial surface and an inner radial surface, and wherein a height of the first fin at the inner radial surface is the same as a height of the inner radial surface.

12. The tongue cleanser according to claim 8, wherein at least one outlet duct communicates with the first vent opening between a rear side of the first fin and the fin base associated with the second fin.

13. The tongue cleanser according to claims 8, wherein the drain channel ends at a lateral edge below the edge that encompasses the substantially disc-shaped body.

14. The tongue cleanser according to claim 6, wherein free ends of the fins have convex bent end surfaces.

15. The tongue cleanser according to claim 1, wherein the end surfaces reside inside a spherically shaped shell surface.

16. The tongue cleanser according to claim 14, wherein the fins are wider in a direction associated with foot-ends of the fins.

17. The tongue cleanser according to claim 16, wherein a width of the first fin continuously increases towards a center of the first fin.

18. The tongue cleanser according to claim 17, wherein each fin is widest nearest to an axial elongation of the hose connection.

19. The tongue cleanser according to claim 6, wherein at least one of a front wall or a rear wall of each fin has a convex bent configuration.

20. The tongue cleanser according to claim 6, wherein at least one of a front wall or a rear wall of each fin has a linearly running configuration.

21. The tongue cleanser according to claim 6, wherein a number of the fins is between four and seven.

22. The tongue cleanser according claim 6, wherein vent openings, including the first vent opening, are provided in an extension direction of the hose connection before and behind the fins.

23. The tongue cleanser according to claim 1, wherein the body also has a plate shape, and a rear side is surpassed by a cylinder nozzle and a conically tapered tube section.

24. The tongue cleanser according to claim 23, wherein the cylinder nozzle is arranged substantially flush with the use-side front surface.

25. The tongue cleanser according to claim 23, wherein the conically tapered tube section ends substantially flush at an end face with an outside contour of the use-side front surface.

26. The tongue cleanser according to claim 1, wherein the body is provided with an insert-molding made of a soft-elastic component at least forming the profiling.

27. The tongue cleanser according to claim 26, wherein the insert-molding forms the profiling as well as a pad arranged at a rear side.

28. The tongue cleanser according to claim 27, wherein a pad is formed of a different soft component than the profiling.

29. The tongue cleanser according to claim 1, wherein a pad comprising nubs is disposed at a rear side of the body.

30. The tongue cleanser according to claim 29, wherein the pad is made of a soft component.

31. The tongue cleanser according to claim 1, wherein the hose connection is formed by a cylinder nozzle surpassing a rear side of the body.

32. The tongue cleanser according to claim 1, wherein the tongue cleanser is produced as a one-piece injection-molded part.

33. A tongue cleanser having a disc-shaped body, an edge that encompasses the disc-shaped body, and a use-side front surface of the edge that is provided with a profiling suitable for superficially scraping impurity adherent to a human tongue, wherein:
  the tongue cleanser forms a hose connection,
  the hose connection communicates with the profiling and merges in longitudinal direction inside the body to form an extending outlet duct,
  the outlet duct communicates with a ventilation opening that is positioned on a surface that is different from the use-side front surface,
  the hose connection, the outlet duct, and the ventilation opening are sequentially arranged in axial direction of a cylinder nozzle, and
  the profiling includes:
    a first fin disposed between a first position on the edge and a second position on the edge that is opposite to the first position;
    a second fin substantially parallel to the first fin and disposed between a third position on the edge and a fourth position on the edge that is opposite to the third position; and
    a drain channel disposed between and parallel to the first fin and the second fin, the drain channel being centrally divided by a vent opening, the vent opening being located below the use-side front surface of the edge, and the drain channel being continuously inclined from the edge to the vent opening.

34. The tongue cleanser according to claim 1, wherein the surface that is different from the use-side front surface comprises a front side end wall.

35. A tongue cleanser having a substantially disc-shaped body, an edge that encompasses the substantially disc-shaped body, and a use-side front surface of the edge that is provided with a profiling suitable for superficially scraping impurity adherent at a human tongue, wherein:
  the profiling includes a drain channel disposed between and parallel to a first fin and a second fin, the drain channel being centrally divided by a first vent opening, the first vent opening being located below the use-side front surface of the edge, and the drain channel being continuously inclined from the edge to the first vent opening.

* * * * *

UNITED STATES PATENT AND TRADEMARK OFFICE
CERTIFICATE OF CORRECTION

PATENT NO. : 11,039,847 B2
APPLICATION NO. : 15/271189
DATED : June 22, 2021
INVENTOR(S) : Matthias Georgi and Christoph Geiberger It is certified that error appears in the above-identified patent and that said Letters Patent is hereby corrected as shown below:

On the Title Page

(63) Related U.S. Application Data:
Please delete "Continuation     of     application    No. PCT/EP2015/055770, filed on Mar. 19, 2015." and insert --Continuation of application No. PCT/EP2015/055770, filed on Mar. 19, 2015.--;

In the Claims

Column 10, Claim 15, Line 24:
Please delete "claim 1" and insert --claim 14--.

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*